United States Patent [19]

Reddy

[11] Patent Number: 5,155,119

[45] Date of Patent: Oct. 13, 1992

[54] 3-(2-PYRIDINYLTHIO)-N-OXIDE, 2-HALO-2-PROPENENITRILE COMPOUNDS USEFUL AS ANTIMICROBIALS

[75] Inventor: Kalakota S. Reddy, Midland, Mich.

[73] Assignee: The Dow Chemical Company, Midland, Mich.

[21] Appl. No.: 846,110

[22] Filed: Mar. 5, 1992

[51] Int. Cl.[5] .................. A01N 37/34; C07D 213/89
[52] U.S. Cl. ..................................... 514/351; 546/300
[58] Field of Search ......................... 546/300; 514/351

[56] References Cited

U.S. PATENT DOCUMENTS

| | | | |
|---|---|---|---|
| 2,745,826 | 5/1956 | Semenoff et al. | 546/361 |
| 3,140,306 | 7/1964 | Heininger | 260/464 |
| 3,236,733 | 2/1966 | Karsten et al. | 514/191 |
| 4,172,892 | 10/1979 | Nannini et al. | 260/464 |
| 4,238,405 | 12/1980 | Felix | 544/26 |
| 4,388,314 | 6/1983 | Nannini et al. | 260/464 |
| 4,529,721 | 7/1985 | Nagata et al. | 514/191 |
| 5,039,702 | 8/1991 | Brandman et al. | 514/526 |

FOREIGN PATENT DOCUMENTS

A20104432  8/1983  European Pat. Off. ............ 260/464

*Primary Examiner*—C. Warren Ivy
*Assistant Examiner*—Zinna Northingtono Davis

[57] ABSTRACT

3-(2-Pyridinylthio-N-oxide, 2-halo-2-propenenitriles are prepared which correspond to the formula:

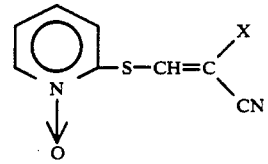

wherein X represents a halogen.

These compounds have been found to exhibit antimicrobial activity in industrial and commercial applications and compositions containing these compounds are so employed.

8 Claims, No Drawings

3-(2-PYRIDINYLTHIO)-N-OXIDE, 2-HALO-2-PROPENENITRILE COMPOUNDS USEFUL AS ANTIMICROBIALS

BACKGROUND OF THE INVENTION

The field of this invention is a novel substituted acrylonitrile compounds which are useful as antimicrobial agents.

U.S. Pat. No. 5,039,702 discloses an α-halo-β-(substituted)thio-acrylonitrile of the formula:

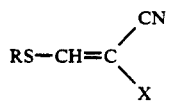

wherein X is a halogen and R is a lower alkyl, aryl, aralkyl, heterocyclo, or a thiocarbonyl group. This compound is taught to be useful as an effective antimicrobial agent.

The desirability of identifying or discovering new antimicrobial agents is widely recognized. New antimicrobial agents are desired for several reasons; these include, but are not limited to, responding to the problem created by the development of microbe strains resistant to known antimicrobials, the occurrence of undesirable interactions of certain known antimicrobials with the medium or product in which the antimicrobial is used, and high toxicity of certain known antimicrobials to certain non-target organisms such as mammals.

The present invention solves these problems by disclosing a new compound which may be employed as an antimicrobial.

SUMMARY OF THE INVENTION

The present invention is a compound corresponding to the formula:

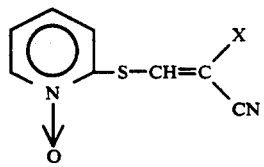

wherein X represents a halogen.

The present invention is also an antimicrobial composition comprising an inert carrier and an antimicrobially effective amount of a compound corresponding to the formula:

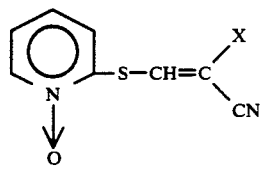

wherein X represents a halogen.

The present invention is also a method for inhibiting microorganisms in a microbial habitat comprising contacting said microbial habitat with an antimicrobially effective amount of a compound corresponding to the formula:

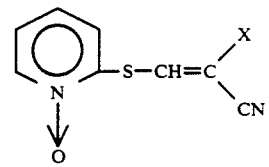

wherein X represents a halogen.

DETAILED DESCRIPTION OF THE INVENTION

The present invention is a compound corresponding to the formula:

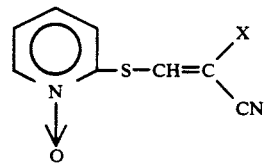

wherein X represents a halogen. Preferably, X represents chlorine or bromine.

The 3-(2-pyridinylthio)-N-oxide, 2-halo-2-propenenitrile compounds of the present invention may be prepared, for example, by the reaction of a 2,3-dihaloacrylonitrile with an alkali salt of 2-mercaptopyridine N-oxide under reactive conditions. Preferably, the 2,3-dihaloacrylonitrile is 2,3-dichloroacrylonitrile. Preferably, the alkali salt of 2-mercaptopyridine N-oxide is the sodium salt of 2-mercaptopyridine N-oxide.

A general reaction scheme for this reaction is as follows:

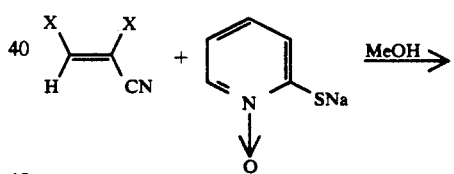

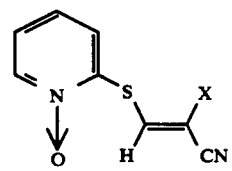

In carrying out this reaction, the 2,3-dihaloacrylonitrile and the sodium salt of 2-mercaptopyridine N-oxide are typically contacted together in substantially equimolar amounts in a suitable solvent. Preferably, the reactions are carried out in an inert solvent such as dimethyl formamide, methanol, acetonitrile, acetone, or pyridine. Preferably, the reactions are carried out at 0° C. under an ambient pressure of inert gas. Subsequent to the addition of the appropriate reaction materials, the reaction mixture is preferably allowed to stir at a temperature of between about 25° C. to about 60° C. for a period of between about 2 to about 24 hours in order to increase the reaction rate and promote extinction of the limiting reagent. Final work-up of the reaction mixture then provides the desired final product.

PREPARATION OF STARTING MATERIALS

The synthesis of 2,3-dihaloacrylonitrile is straightforward and is described in the art. Typically, the synthesis of 2,3-dichloroacrylonitrile begins with the chlorination of acrylonitrile to form 2,2,3-trichloropropionitrile. This chlorination is straightforward and is described in the art, such as in N. C. Lorette, "The Addition of Chlorine to Acrylonitrile", *J. Org. Chem.*, Vol. 26, pp. 2324–2327, 1960. Overall yields of over 90 percent based on acrylonitrile are achievable.

Dehydrochlorination of 2,2,3-trichloropropionitrile yields an isomeric mixture of 2,3-dichloroacrylonitrile. This dehydrochlorination can be carried out by heating the 2,2,3-trichloropropionitrile in the presence of a catalyst. Purification of the 2,3-dichloroacrylonitrile prior to subsequent reaction is optional. This dehydrochlorination is straightforward and is described in the art, such as in U.S. Pat. No. 2,385,550 or U.S. Pat. No. 3,527,787.

The synthesis of the sodium salt of 2-mercaptopyridine N-oxide is straightforward and is described in the art, such as in U.S. Pat. Nos. 2,745,826 and 3,236,733.

The following examples illustrate the present invention and the manner by which it can be practiced but, as such, should not be construed as limitations upon the overall scope of the same.

EXAMPLE 1

Preparation of 3-(2-Pyridinylthio)-N-Oxide, 2-Chloro-2-Propenenitrile

To a 250 mL three-neck round bottom flask fitted with an addition funnel, a thermometer and a positive pressure nitrogen inlet are added 2,3-dichloroacrylonitrile (5.0 g, 0.04 moles) and methanol (60 mL). The reaction mixture is stirred at 0° C. for five minutes and then the methanolic solution of the sodium salt of 2-mercaptopyridine N-oxide (sodium omadine) (6.10 g, 0.04 moles in 60 mL of methanol) is added slowly dropwise over 25 to 35 minutes. The resultant mixture is stirred at below 5° C. for one hour followed by 4 hours at room temperature. The progress of the reaction is monitored by gas chromatography analysis. The precipitate is filtered, washed with water, methanol and dried under vacuum to give the product as a white crystalline solid (6.0 g, yield is 76 percent). The product is a mixture of Z- and E-isomers.

The structure identity is confirmed by proton nuclear magnetic resonance spectroscopy, carbon nuclear magnetic resonance spectroscopy, infrared spectroscopy and gas chromatography/mass spectrometry.

ANTIMICROBIAL ACTIVITY

The compounds of this invention are useful as antimicrobial additives to such industrial products as styrene-butadiene latexes used for paper coatings, paints, inks, adhesives, soaps, cutting oils, textiles, and paper and pigment slurries. The compounds are also useful as antimicrobial additives in such personal care products as hand creams, lotions, shampoos, and hand soaps. A further advantage of this invention is its cost-effectiveness for applications which need to have an antimicrobial continuously replenished, such as in cooling towers and pulp and paper mills.

As appreciated in the art, the compounds disclosed herein are not necessarily active at the same concentration against different microbial species. That is, there is some microorganism-to-microorganism variation in antimicrobial potency and spectrum of antimicrobial activity.

The present invention is also directed to a method for inhibiting microorganisms which comprises contacting said microorganisms or habitat thereof with an effective amount of the compounds of this invention.

The antimicrobial compound of this invention may be added directly to aqueous formulations susceptible to microbial growth, either undiluted or dissolved in organic solvents such as glycols, alcohols, or acetone. The compound may also be added alone or in combination with other perservatives.

As used herein, the term "microorganism" is meant to refer to bacteria, fungi, viruses, algae, subviral agents and protozoa.

As used herein, the term "antimicrobially effective amount" refers to that amount of one or a mixture of the compounds, or of a composition comprising such compound or compounds, of this invention needed to exhibit inhibition of selected microorganisms. Typically, this amount varies from providing about 1 part per million (ppm) to about 5,000 ppm by weight of the compound to a microbial habitat being contacted with the compound. Such amounts typically vary depending upon the particular microorganism treated and the conditions under which such microorganism or microbial habitat is treated. Also, the exact concentration of the compound to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weight, of a microbial habitat.

The term "microbial habitat" refers to a place or type of site where a microorganism naturally or normally lives or grows. Typically, such a microbial habitat will be an area that comprises a moisture, nutrient, and/or an oxygen source such as, for example, a cooling water tower or an air washing system.

The terms "inhibition", "inhibit" or "inhibiting" refer to the suppression, stasis, kill, or any other interference with the normal life processes of microorganisms that is adverse to such microorganisms, so as to destroy or irreversibly inactivate existing microorganisms and/or prevent or control their future growth and reproduction.

The antimicrobial activity of the compound of the present invention is demonstrated by the following techniques.

The minimum inhibitory concentration (MIC) for the compound of this invention is determined for 9 bacteria, using nutrient agar, and 7 yeast and fungi, using malt yeast agar. A one percent solution of the compound is prepared in a mixture of acetone and water. Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04M solution of N-[tris-(hydroxymethyl)methyl]-glycine buffered deionized water with concentrated sodium hydroxide to a pH of 8.5. Malt yeast agar is prepared by adding 3 g yeast extract and 45 g malt agar per liter of deionized water. The specific agar is dispensed in 30 ml aliquots into 25×200 mm test tubes, capped and autoclaved for 15 minutes at 115° C. The test tubes containing the agar are cooled in a water bath until the temperature of the agar is 48° C. Then, an appropriate amount of the one percent solution of the compound is added (except in the controls where no compound is added) to the respective test tubes so that the final concentrations are 500, 250, 100, 50, 25, 10, 5, 2.5, 1.0 and zero parts per million of the compound in the agar, thus having a known concentration of compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per ml of suspension of a particular bacteria. Aliquots of 0.3 ml of each of the bacterial suspensions are used to fill the individual wells of Steer's Replicator. For each microbial suspension, 0.3 ml was used to fill three wells (i.e., three wells of 0.3 ml each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 ml of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension: 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table I lists the bacteria, yeast and fungi used in the MIC test described above along with their respective American Type Culture Collection (ATCC) identification numbers.

TABLE I

Organisms used in the Minimum Inhibitory Concentration Test

| Organism | ATCC No. |
| --- | --- |
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Sc) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

In Tables II and III, the MIC values of the compound as compared to the MIC of a standard commercial preservative (DOWICIL ™ 75, a trademark of The Dow Chemical Company, with 1-(3-chloroallyl)-3,5,7-triaza-1-azoniaadamantane chloride as the active agent) are set forth for the bacteria organisms and yeast/fungi organisms which are listed in Table I. As can be seen from Tables II and III, the 3-(2-pyridinylthio)-N-oxide, 2-chloro-2-propenenitrile compound generally achieves better antimicrobial results than the standard commercial preservative. With such antimicrobial activity, the 3-(2-pyridinylthio)-N-oxide, 2-chloro-2-propenenitrile compound should have the ability to serve as a preservative in a variety of formulated industrial, household, and commercial products such as latex, tape joint, hand lotion, and shampoo compositions.

TABLE II

Minimum Inhibitory Concentrations for Test Compounds in Bacteria Species (in ppm)

| Compound | ORGANISMS | | | | | | | | |
| --- | --- | --- | --- | --- | --- | --- | --- | --- | --- |
| | Bs | Ea | Ec | Kp | Pv | PRD | Pa | Sc | Sa |
| DOWICIL ™ 75 | | | | | | | | | |
| pH 6.8 | 50 | 100 | 100 | 50 | 50 | 100 | 100 | 50 | 100 |
| pH 8.2 | 250 | 250 | 250 | 250 | 250 | 500 | >500 | 100 | 250 |
| 3-(2-pyridinylthio)-N-oxide, 2-chloro-2-propenenitrile | | | | | | | | | |
| pH 6.8 | 25 | 250 | 50 | 100 | 50 | >50 | >500 | 25 | 25 |
| pH 8.2 | 25 | 250 | 100 | 100 | 100 | 500 | >500 | 100 | 50 |

TABLE III

Minimum Inhibitory Concentrations for Test Compounds in Yeast/Fungi Species (in ppm)

| COMPOUND | ORGANISMS | | | | | | |
| --- | --- | --- | --- | --- | --- | --- | --- |
| | An | Ca | Pc | Sc | Tv | Ap | Fo |
| DOWICIL ™ 75 | >500 | >500 | >500 | 500 | >500 | >500 | >500 |
| 3-(2-pyridinylthio)-N-oxide, 2-chloro- | 250 | 500 | 50 | 250 | 250 | — | 50 |

TABLE III-continued

Minimum Inhibitory Concentrations for Test Compounds in Yeast/Fungi Species (in ppm)

| COMPOUND | ORGANISMS | | | | | | |
|---|---|---|---|---|---|---|---|
| | An | Ca | Pc | Sc | Tv | Ap | Fo |
| 2-propenenitrile | | | | | | | |

What is claimed is:

1. A compound corresponding to the formula:

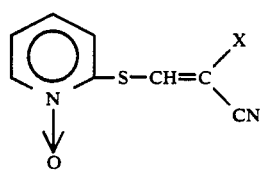

wherein X represents a halogen.

2. The compound of claim 1 wherein X represents chlorine.

3. An antimicrobial composition comprising an inert carrier and an antimicrobially effective amount of a compound corresponding to the formula:

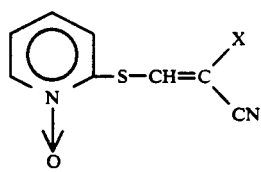

wherein X represents a halogen.

4. The composition of claim 3 wherein X represents chlorine.

5. The composition of claim 3 wherein the compound is present in the composition in an amount to provide from about 1 part per million to about 5,000 parts per million by weight of the compound to a microbial habitat that is contacted with the composition.

6. A method for inhibiting microorganisms in a microbial habitat comprising contacting said microbial habitat with an antimicrobially effective amount of a compound corresponding to the formula:

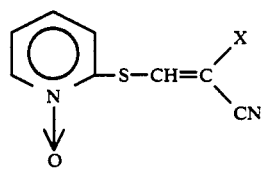

wherein X is a halogen.

7. The method of claim 6 wherein the compound is present in an amount to provide from about 1 part per million to about 5,000 parts per million by weight of the compound to the microbial habitat.

8. The method of claim 6 wherein X represents chlorine.

* * * * *